United States Patent [19]

Kim

[11] Patent Number: 5,133,964
[45] Date of Patent: Jul. 28, 1992

[54] PHARMACEUTICAL LIQUID COMPOSITION CONTAINING BEZOAR BOVIS AND PREPARATION FOR ITS MANUFACTURE

[76] Inventor: Young S. Kim, Cosmos Mansion 1002, #302-62, Ichon-Dong, Yongsan-Ku, Seoul, Rep. of Korea

[21] Appl. No.: 595,671

[22] Filed: Oct. 11, 1990

Related U.S. Application Data

[63] Continuation of Ser. No. 171,432, Mar. 21, 1988, abandoned.

[30] Foreign Application Priority Data

Jul. 9, 1987 [KR] Rep. of Korea .............. 87-6998[U]

[51] Int. Cl.$^5$ ........................................... H61K 35/78
[52] U.S. Cl. ................................ 424/195.1; 424/520; 424/551
[58] Field of Search ............... 424/195.1, 520, 551

[56] References Cited

PUBLICATIONS

Steinmetz, Codex Vegetabilis, ref. Nos. 99, 209, 304, 403, 524–525, 788–789, 800, 907, 1042, 1215–1216, (1957).

Primary Examiner—John W. Rollins
Attorney, Agent, or Firm—Birch, Stewart, Kolasch & Birch

[57] ABSTRACT

A pharmaceutical liquid composition prepared by combining a predetermined quantity of natural substances from the genera Glycyrrhizae Radix, Ginseng Radix, Typhae Pollen, Massa Medicata Fermentata, Sojae germinatum Semen, Cinnamomi Cortex, Paeoniae Radix, Liriope Tuber, Scutellariae Radix, Angelicae Gigantis Radix, Ledebouriellae Radix, Atractylodis Rhizoma Alba, Bupleuri Radix, Platycodi Radix, Armeniacae Semen, Hoelen, Cnidii Rhizoma, Antellopis Cornu, Ampelopsis Radix, Zingiberis Rhizoma, and Dioscoreae Rhizoma and cutting the natural substances into microparticle size or extracting the natural substances with water or alcohol to form a first microparticle product or extracts; providing a predetermined quantity of natural substances from the genera Bezoar Bovis, Moschus, and Borneol and cutting the natural substances into microparticle size to form a second microparticle product; providing a Gelatin solution; mixing the first microparticle product or extract with the second microparticle product and Gelatin solution; and preparing the mixture with water or alcohol to produce a pharmaceutical liquid composition for orally administering to patients such as infants, children, critical patients, and the like.

4 Claims, No Drawings

PHARMACEUTICAL LIQUID COMPOSITION CONTAINING BEZOAR BOVIS AND PREPARATION FOR ITS MANUFACTURE

This application is a continuation of application Ser. No. 07/171,432, filed on Mar. 21, 1988, which is now abandoned.

BACKGROUND OF THE INVENTION

1. Field of the Invention

The present invention relates generally to a novel pharmaceutical liquid composition containing *Bezoar Bovis* for for treating patients suffering from stroke, arteriosclerosis, hypertension, tachycardia, dyspnea, anxiety, cardiostenosis, acute and chronic convulsions, automatic nervous system disease, and coma, and to a preparation method for its manufacture. More particularly, the present invention relates to the preparation of oral and parental natural substance liquids of improved physical stability.

2. Description of the Prior Art

Examples of known solid composition preparations obtained from natural substances include, for example, a *Bezoar Bovis* pill containing 45 mg of *Bezoar Bovis*, 263 mg of *Dioscoreae Rhizoma*, 188 mg of *Glycyrrhizae Radix*, 94 mg of *Ginseng Radix*, 94 mg of *Typhae Pollen*, 94 mg of *Massa Medicata Fermentata*, 66 mg of *Sojae germinatum Semen*, 66 mg of *Cinnamomi Cortex*, 66 mg of Gelatin, 56 mg of *Paeoniae Radix*, 56 mg of *Liripe Tuber*, 56 mg of *Scutellariae Radix*, 56 mg of *Angelicae Gigantis Radix*, 56 mg of *Ledebouriellae Radix*, 56 mg of *Atractylodis Rhizoma Alba*, 47 mg of *Bupleuri Radix*, 47 mg of *Platycodi Radix*, 47 mg of Armeniacae Semen, 47 mg Hoelen, 47 mg of *Cnidii Rhizoma*, 38 mg of *Antellopis Cornu*, 38 mg of Moschus, 38 mg of Borneol, 28 mg of *Ampelopsis Radix*, and 28 mg of *Zingiberis Rhizoma*. However, such prior art *Bezoar Bovis* pills suffer from many disadvantages such as, for example, it is not feasible for patients in critical condition to orally and parentally administer these pills nor for infants and children to orally and parentally administer them. Furthermore, these pills do not provide for treatment of the illness of a patient in a fast manner.

SUMMARY OF INVENTION

Accordingly, it is an object of the present invention to provide a pharmaceutical liquid composition such as gel or sol preparation which is a mixture of natural substances including *Bezoar Bovis*, *Dioscoreae Rhizoma*, *Glycyrrhizae Radix*, *Ginseng Radix*, *Typhae Pollen*, *Massa Medicata Fermentata*, *Sojae germinatum Semen*, *Cinnamomi Cortex*, Gelatin, *Paeoniae Radix*, *Liriope Tuber*, *Scutellariae Radix*, *Angelicae Gigantis Radix*, *Ledebouriellae Radix*, *Atractylodis Rhizoma Alba*, *Bupleuri Radix*, *Platycodi Radix*, *Armeniacae Semen*, Hoelen, *Cnidii Rhizoma*, *Antellopis Cornu*, Moschus, Borneol, *Ampelopsis Radix*, and *Zingiberis Rhizoma* for easy oral and parental administration thereof to critical patients.

Another object of the present invention is to provide a pharmaceutical liquid preparation from the above-identified natural substances for providing medication to infants and children.

A further object of the present invention is to provide a preparation method for manufacturing a pharmaceutical liquid composition containing ox *Bezoar Bovis* for cleaning a patient's chest.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

The present invention pertains to a pharmaceutical liquid composition prepared by a process which comprises providing a predetermined quantity of natural substances from the genera *Dioscoreae Rhizoma*, *Glycyrrhizae Radix*, *Ginseng Radix*, *Typhae Pollen*, *Massa Medicata Fermentata*, *Sojae germinatum Semen*, *Cinnamomi Cortex*, *Paeoniae Radix*, *Liriope Tuber*, *Scutellariae Radix*, *Angelicae Gigantis Radix*, *Ledebouriellae Radix*, *Atractylodis Rhizoma Alba*, *Bupleuri Radix*, *Platycodi Radix*, *Armeniacae Semen*, Hoelen, *Cnidii Rhizoma*, *Antellopis Cornu*, *Ampelopsis Radix*, and *Zingiberis Rhizoma*; cutting the natural substances into a microparticle size and/or extracting the natural substances with water or alcohol to form a first microparticle product or extract; providing a predetermined quantity of natural substances from the genera *Bezoar Bovis*, Moschus, and Borneol; cutting the natural substances into a microparticle size to form a second microparticle product; providing a genus Gelatin solution; mixing the first microparticle product or extract with the second microparticle product and the Gelatin solution to form a mixture; and preparing the mixture with water or alcohol to produce a pharmaceutical liquid composition for orally administering to patients such as infants, children, critical patients, and the like.

DETAILED DESCRIPTION OF PREFERRED EMBODIMENT

Referring now in detail to the present invention, there is provided a pharmaceutical liquid composition, the composition being made from natural substances, namely, the genera *Bezoar Bovis*, *Dioscoreae Rhizoma*, *Glycyrrhizae Radix*, *Ginseng Radix*, *Typhae Pollen*, *Massa Medicata Fermentata*, *Sojae germinatum Semen*, *Cinnamomi Cortex*, Gelatin, *Paeoniae Radix*, *Liriope Tuber*, *Scutellariae Radix*, *Angelicae Gigantis Radix*, *Ledebouriellae Radix*, *Atractylodis Rhizoma Alba*, *Bupleuri Radix*, *Platycodi Radix*, *Armeniacae Semern*, Hoelen, *Cnidii Rhizoma*, *Antellopis Cornu*, Moschus, Borneol, *Ampelopsis Radix*, and *Zingiberis Rhizoma*. Before the cutting or extracting the natural substances, the genera *Bezoar Bovis*, *Dioscoreae Rhizoma*, *Glycyrrhizae Radix*, *Ginseng Radix*, *Typhae Pollen*, *Massa Medicata Fermenaata*, *Sojae germinatum Semen*, *Cinnamomi Cortex*, Gelatin, *Paeoniae Radix*, *Liriopsis tuber*, *Scutellariae Radix*, *Angelicae Gigantis Radix*, *Ledebouriellae Radix*, *Atractylodis Rhizoma Alba*, *Bupleuri Radix*, *Platycodi Radix*, *Armeniacae Semen*, Hoelen, *Cnidii Rhizoma*, *Antellopis Cornu*, Moschus, Borneolum, *Ampelopsis Radix*, and *Zingiberis Rhizoma* are mixed together in a predetermined weight ratio. First of all, 263 g of *Dioscoreae Rhizoma*; 188 g of *Glycyrrhizae Radix*; 94 g of *Ginseng Radix*, *Typhae Pollen*, and *Massa Medicata Fermentata*; 66 g of *Sojae germinatum Semen* and *Cinnamomi Cortex*; 56 g of *Paeoniae Radix*, *Liriope Tuber*, *Scutellariae Radix*, *Angelicae Gigantis Radix*, *Ledebouriellae Radix*, and *Atractylodis Rhizoma Alba*; 47 g of *Bupleuri Radix*, *Platycodi Radix*, *Armeniacae Semen*, Hoelen, and *Cnidii Rhizoma*; 38 g of *Antellopis Cornu*;

and 28 g of *Ampelopsis Radix* and *Zingiberis Rhizoma* are cut into microparticle size or extracted with water or alcohol to form a first microparticle product or extract. Secondly, 45 g of *Bezoar Bovis;* 38 g of Moschus and Borneolum, are cut into microparticle size to produce a second microparticle product. Thirdly, 66 g of Gelatin is added to distilled water at an elevated temperature to produce a Gelatin solution.

The above-produced first microparticle product or extract, second microparticle product and Gelatin solution are then mixed together with water or alcohol to produce a pharmaceutical liquid composition for orally administering to patients. At this time, if necessary, a perservative, sweetening agent, stabilizer, solvent, emulsifier, colloidifier, aromatic agent, or the like can be added and mixed with the above-resulted liquid composition.

The various species of the genera of natural substances found to be useful for the pharmaceutical composition of the present invention are Bos taurus var domesticus Gmelin of *Bezoar Bovis*, *Glycyrrhiza glabra Linne var grandifera* or *Glycyrrhiza uratensis* of *Glycyrrhizae Radix*, *Panax schinseng Nees* of *Ginseng Radix*, *Typhar orientalis presl* of *Typhae Pollen*, *Glycine max Merril* of *Sojae germinatum Semen*, *Cinnamomum Cassia* of *Cinnamomi Cortex*, *Paeonia albiflora pallas var. trichocarpa* of *Paeoniae Radix*, *Liriope platyphylla wang et Tang* of *Liriope Tuber*, *Scutellaria baicalensis Georgi* of *Scutellariae Radix*, *Angelica gigas Nakai* of *Angelicae Gigantis Radix*, *Ledebouriella seseloides Wolff* of *Ledebouriellae Radix*, *Atractylodes japonica Koidzumi* of *Atractylodis Rhizoma Alba*, *Bupleurum falcatum Linne* of *Bupleuri Radix*, *Platycodon grandiflorum A de Candolle* of *Platycodi Radix*, *Prunus armeniaca Linne var. ansu Maximowicz* or *P. mandshurica Kochne var. glabra Nakai* of *Armeniacae Semen*, *Poria cocos Wolf* of Hoelen, *Cnidium officinale Makino* of *Cnidii Rhizoma*, *Gazella subgutturosa Guldenstaedt* of *Antellopis Cornu*, *Moschus moschiferus Linne* of Moschus, *Dryobalanops aromatica Gaertner* of Borneol, *Ampelopsis japonica Makino* of *Ampelopsis Radix*, *Zingiber officinale Roscoe* of *Zingiberis Rhizoma*, and *Dioscorea japonica Thumberg* of *Dioscoreae Rhizoma*.

Preservatives useful according to the present invention include p-oxybenzoic propyl ester (propyl-p-ben) p-oxybenzoic methyl ester (methyl-p-ben), sodium phosphoric benzoate, and the like.

Sweetening agents useful in accordance with the present invention include honey, sugar, sorbitol, saccharine, ASPARTAME, 3-amino-N-(α-carboxyphenethyl)succinamic acid N-methyl ester, and the like.

Solvents useful for the present invention include distilled water, ethanol, and the like.

Colloidal agents and emulsifiers which may be used include sodium carboxymethylcellulose, pectin, agar, alganic acid, and the like.

Useful aromatic agents include menthol, cinnamomi cortex, orange perfume, and the like.

The present invention will now be described in more detail in connection with the following examples which should be considered as being exemplary and not limiting the present invention.

EXAMPLE 1

263 g of *Dioscoreae Rhizoma;* 188 g of *Glycyrrhizae Radix;* 94 g of *Ginseng Radix, Typhae Pollen*, and *Massa Medicata Fermentata;* 66 g of *Sojae germinatum Semen* and *Cinnamomi Cortex;* 56 g of *Paeoniae Radix, Liriope Tuber, Scutellariae Radix, Angelicae Gigantis Radix, Ledebouriellae Radix*, and *Atractylodis Rhizoma Alba;* 47 g of *Bupleuri Radix, Platycodi Radix, Armeniacae Semen,* Hoelen, and *Cnidii Rhizoma;* 38 g of *Antellopis Cornu;* and 28 g of *Ampelopsis Radix* and *Zingiberis Rhizoma*, are cut into microparticle size by a cutting apparatus. Then 7.5 liters of water are added to approximately 1.5 Kg of the natural substance mixture in an extractor. The mixture in the extractor is stirred and condensed. Thereafter, the aqueous mixture is filtered and residues from the first filtration are again filtered. Both filtrates are condensed for about 2 hours to produce a natural substance extract.

45 g of *Bezoar Bovis;* 38 g of Moschus and Borneol; and 30 g of carboxycellulose are ground into microparticle size in a grinder to form a microparticle mixture. Then 200 ml of water, QS (Quantum Sufficit), about 50 ml of ethanol and 5 g of methanol are added to the microparticle mixture to produce a *Bezoar Bovis* solution. 10 Kg of sugar and 1 Kg of solbitol or 1 Kg of ASPARTAME, 3-amino-N-(α-carboxyphenethyl)succinamic acid N-methyl ester, are solved QS with distilled water to make a sweetening solution which is added to the *Bezoar Bovis* liquid to produce a first *Bezoar Bovis* mixture.

100 ml of distilled water is added to 66 g of the genus Gelatin and the aqueous mixture is heated to produce a Gelatin liquid.

In addition, 45 g of *Bezoar Bovis*, 38 g of Moschus, and 300 g of carboxycellulose are ground into microparticle size to form a microparticle product and 200 ml of distilled water is added to the microparticle product to produce a *Bezoar Bovis* solution. 50 ml of ethanol and 5 g of methanol are added to 38 g of the genus Borneol to produce Borneol solution. Then, the *Bezoar Bovis* solution and the Borneol solution are mixed to form a second *Bezoar Bovis* mixture.

The above-produced products, that is the natural substance extract, the first and second Bezoar mixtures, and the Gelatin solution are mixed together with distilled water to a 30 liter volume. Thereafter, the mixture is stirred uniformly to produce a pharmaceutical liquid product for orally and parentally administering to patients. The final pharmaceutical liquid product can be prepared as a gel, sol, or a like preparation for easy administration and so as to simplify packaging.

EXAMPLE 2

The pre-extraction procedures in forming the natural substance mixture in Example 1 are repeated. Then 7.5 liters of ethanol are added to the natural substance mixture at a cold temperature and the extract allowed to stand for about 10 days. The mixture is filtered and QS distilled water is added to the filtrate to make a natural substance extract.

The procedures for making the first and second *Bezoar Bovis* mixtures and the Gelatin solution of Example 1 are repeated. The natural substance extract, *Bezoar Bovis* mixtures, and Gelatin solution are mixed and added to 30 liters of purified water for use as a pharmaceutical, oral liquid.

EXPERIMENT 1

The present Experiment 1 is the data resulting from experimentation of the pharmaceutical liquid according to the present invention. A 30 ml sample prepared from Example 1 is used in the following tests for determining the respective amounts of (a) active bilirubin at a temperature of 30° C. and 60° C. (Table 1), (b) active bilirubin in direct sunlight and in a room wherein the sun rays are scattered (Table 2), and active bilirubin after a long period of storage (Table 3) as follows:

TABLE 1

| Lot No. | Period | Condition 30° C. | | | | | Condition 60° C. | | | | |
|---|---|---|---|---|---|---|---|---|---|---|---|
| | | Result (Remarks) | pH | Density | Viscosity | Content | Result (Remarks) | pH | Density | Viscosity | Content |
| SU-83001 | Beginning | Suitability | 4.819 | 1.130 | 20.62 | 189.6 | Suitability | 4.819 | 1.103 | 20.61 | 189.6 |
| | 2 (Months) | " | 4.818 | 1.131 | 20.61 | 190.1 | " | 4.819 | 1.131 | 20.54 | 189.6 |
| | 4 (Months) | " | 4.817 | 1.130 | 20.64 | 188.6 | " | 4.818 | 1.132 | 20.55 | 188.4 |
| | 6 (Months) | " | 4.816 | 1.132 | 20.65 | 188.2 | " | 4.816 | 1.131 | 20.57 | 187.0 |
| SU-83002 | Beginning | " | 4.821 | 1.130 | 20.52 | 189.8 | " | 4.821 | 1.130 | 20.52 | 189.8 |
| | 2 (Months) | " | 4.820 | 1.130 | 20.55 | 189.3 | " | 4.822 | 1.128 | 20.55 | 190.1 |
| | 4 (Months) | " | 4.818 | 1.131 | 20.56 | 189.2 | " | 4.186 | 1.131 | 20.35 | 188.2 |
| | 6 (Months) | " | 4.819 | 1.131 | 20.58 | 187.4 | " | 4.818 | 1.131 | 20.57 | 188.3 |
| SU-83003 | Beginning | " | 4.817 | 1.131 | 20.63 | 190.2 | " | 4.817 | 1.131 | 20.63 | 190.2 |
| | 2 (Months) | " | 4.819 | 1.132 | 20.63 | 190.2 | " | 4.817 | 1.130 | 20.52 | 188.4 |
| | 4 (Months) | " | 4.817 | 1.131 | 20.65 | 190.0 | " | 4.818 | 1.132 | 20.56 | 187.9 |
| | 6 (Months) | " | 4.816 | 1.132 | 20.66 | 187.8 | " | 4.816 | 1.132 | 20.58 | 186.9 |

TABLE 2

| Condition | Period | Lot No. SU-83001 | | | | | Lot No. SU-83002 | | | | |
|---|---|---|---|---|---|---|---|---|---|---|---|
| | | Result (Remarks) | pH | Density | Viscosity | Content | Result (Remarks) | pH | Density | Viscosity | Content |
| Direct Ray | Beginning | Suitability | 4.819 | 1.130 | 20.62 | 189.6 | Suitability | 4.821 | 1.130 | 20.52 | 188.8 |
| | 1 Day | " | 4.821 | 1.130 | 20.63 | 188.2 | " | 4.818 | 1.132 | 20.49 | 190.4 |
| | 3 Days | " | 4.817 | 1.131 | 20.61 | 188.9 | " | 4.820 | 1.131 | 20.52 | 188.4 |
| | 5 Days | " | 4.818 | 1.131 | 20.61 | 188.2 | " | 4.816 | 1.132 | 20.54 | 185.8 |
| Scattering Ray | Beginning | " | 4.812 | 1.130 | 20.62 | 189.6 | " | 4.821 | 1.130 | 20.52 | 189.8 |
| | 5 Days | " | 4.816 | 1.130 | 20.63 | 189.5 | " | 4.820 | 1.132 | 20.51 | 188.6 |
| | 10 Days | " | 4.819 | 1.131 | 20.61 | 188.6 | " | 4.818 | 1.131 | 20.53 | 189.2 |
| | 20 Days | " | 4.822 | 1.130 | 20.62 | 189.6 | " | 4.817 | 1.133 | 20.54 | 187.7 |
| | 30 Days | " | 4.817 | 1.131 | 20.63 | 187.2 | " | 4.819 | 1.132 | 20.57 | 187.3 |

| Condition | Period | Lot No. SU-83003 | | | | |
|---|---|---|---|---|---|---|
| | | Result (Remarks) | pH | Density | Viscosity | Content |
| Direct Ray | Beginning | Suitability | 4.817 | 1.131 | 20.63 | 190.2 |
| | 1 Day | " | 4.821 | 1.131 | 20.55 | 190.1 |
| | 3 Days | " | 4.818 | 1.132 | 20.64 | 189.1 |
| | 5 Days | " | 4.817 | 1.132 | 20.64 | 187.7 |
| Scattering Ray | Beginning | " | 4.817 | 1.131 | 20.63 | 190.2 |
| | 5 Days | " | 4.820 | 1.132 | 20.61 | 188.9 |
| | 10 Days | " | 4.817 | 1.132 | 20.63 | 189.3 |
| | 20 Days | " | 4.818 | 1.132 | 20.65 | 188.4 |
| | 30 Days | " | 4.816 | 1.133 | 20.64 | 187.8 |

TABLE 3

| Condition | Period | Lot No. SU-83001 | | | | | Lot No. SU-83002 | | | | |
|---|---|---|---|---|---|---|---|---|---|---|---|
| | | Result (Remarks) | pH | Density | Viscosity | Content | Result (Remarks) | pH | Density | Viscosity | Content |
| Long Period | Beginning | Suitability | 4.819 | 1.130 | 20.62 | 189.6 | Suitability | 4.821 | 1.130 | 20.51 | 188.8 |
| | 3 (Months) | " | 4.819 | 1.131 | 20.63 | 189.9 | " | 4.820 | 1.131 | 20.52 | 189.7 |
| | 6 (Months) | " | 4.818 | 1.129 | 20.62 | 188.4 | " | 4.811 | 1.132 | 20.56 | 190.2 |
| | 9 (Months) | " | 4.821 | 1.131 | 20.65 | 190.1 | " | 4.818 | 1.129 | 20.55 | 188.6 |
| | 12 (Months) | " | 4.818 | 1.129 | 20.65 | 188.5 | " | 4.816 | 1.131 | 20.54 | 187.7 |
| | 18 (Months) | " | 4.817 | 1.133 | 20.64 | 187.7 | " | 4.817 | 1.132 | 20.54 | 186.9 |
| | 24 (Months) | " | 4.818 | 1.131 | 20.65 | 186.0 | " | 4.816 | 1.131 | 20.57 | 185.0 |

| Condition | Period | Lot No. SU-83003 | | | | |
|---|---|---|---|---|---|---|
| | | Result (Remarks) | pH | Density | Viscosity | Content |
| Long Period | Beginning | Suitability | 4.818 | 1.131 | 20.63 | 190.2 |
| | 3 (Months) | " | 4.818 | 1.132 | 20.62 | 190.2 |
| | 6 (Months) | " | 4.821 | 1.131 | 20.61 | 188.6 |
| | 9 (Months) | " | 4.819 | 1.130 | 20.64 | 188.9 |
| | 12 (Months) | " | 4.818 | 1.132 | 20.64 | 186.5 |
| | 18 (Months) | " | 4.819 | 1.133 | 20.56 | 187.4 |

TABLE 3-continued

| | | | | 4.816 | 1.132 | 20.67 | 185.8 |
| --- | --- | --- | --- | --- | --- | --- | --- |
| | 24 (Months) | " | | | | | |

EXPERIMENT 2

1. Procedure

This method was designed to evaluate activity based on the oral administration of the pharmaceutical liquid from the Example 1 to animals. The animals used in this test were male and female Sprague Dawley rats who were 7–8 weeks old and weighted 220+20 g, and male and female Day mice who were 6–7 weeks old and weighed 20+2.0 g and 18+2.0 g, respectively. Before performing this test, the animals were fed solid feed stuffs at a temperature of 24+2° C. and a moisture of 65+5%. 7 days prior to test initiation, the pharmaceutical liquid of the present invention was orally administrated to the animals. A group has 10 animals.

2. Results

The results obtained from the toxic activity test of the pharmaceutical liquid of the present invention are shown in Tables 4 (Rats) and 5 (Mice) as follows:

TABLE 4

| Sex | Dosage (ml/kg) | 1 (Day) | 2 (Days) | 3 (Days) | 4 (Days) | 5 (days) | 6 (Days) | 7 (Days) | Fetal % | $LD_{50}$ |
| --- | --- | --- | --- | --- | --- | --- | --- | --- | --- | --- |
| Male | 15 | 0/10 | | | | | | 0/10 | | |
| | 30 | " | | | | | | | | |
| | 45 | " | | | | | | | | |
| | 60 | " | | | | | | | | |
| | 75 | " | | | | 1/10 | | 1/10 | 10 | |
| Female | 15 | 0/10 | | | | | | 0/10 | | |
| | 30 | " | | | | | | " | | |
| | 45 | " | | | | | | " | | |
| | 60 | " | | | | | | " | | |
| | 75 | " | | | | | | " | | |

TABLE 5

| Sex | Dosage (ml/kg) | 1 (Day) | 2 (Days) | 3 (Days) | 4 (Days) | 5 (days) | 6 (Days) | 7 (Days) | Fetal % | $LD_{50}$ |
| --- | --- | --- | --- | --- | --- | --- | --- | --- | --- | --- |
| Male | 70 | 0/10 | | | | 2/10 | | 2/10 | 20 | |
| | 80 | " | | | | 2/10 | | 3/10 | 30 | |
| | 90 | " | 1/10 | | 2/10 | | | 5/10 | 50 | |
| | 100 | " | | 3/10 | 5/10 | | 7/10 | | 8/10 | 80 | |
| | 110 | " | 2/10 | 4/10 | 5/10 | 7/10 | 10/10 | 10/10 | 100 | 109.6 |
| Female | 70 | 0/10 | | | | | | | 0 | – |
| | 80 | " | | | | 1/10 | 2/10 | 2/10 | 20 | |
| | 90 | " | | 2/10 | | 4/10 | | 4/10 | 40 | |
| | 100 | " | | 2/10 | 4/10 | 7/10 | 8/10 | 8/10 | 80 | |
| | 110 | " | | 3/10 | 5/10 | 8/10 | 9/10 | 10/10 | 100 | 109.6 |

In the Table 5, the mice that were treated with a 110 ml/kg dosage were killed. However, the mice treated with $LD_{50}$ at 109.6 ml/kg of average dosage lived.

Accordingly, the results from Tables 4 and 5 indicate suitable toxic activity with the pharmaceutical liquid of the present invention.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A process for preparing a pharmaceutical liquid composition, which comprises the steps of:
   (a) extracting a first microparticle mixture of *Dioscoreae Rhizoma, Glycyrrhizae Radix, Ginseng Radix, Typhae Pollen, Massa Medicata Fermenta, Sojae germinatum Semen, Cinnamomi Cortex, Paeoniae Radix, Liriope Tuber, Scutellariae Radix, Angelicae Gigantis Radix, Ledebouriellae Radix, Atractylodis Rhizoma Alba, Bupleuri Radix, Platycodi Radix, Armeniacae Semen, Hoelen, Cnidii Rhizoma, Antellopis Cornu, Ampelopsis Radix,* and *Zingiberis Rhizoma* and extracting said first microparticle mixture with water to provide a first extract and filtering said first extract to provide a first filtrate,
   (b) combining a second microparticle mixture of *Benzoar Bovis, Moschus,* and *Borneol* with ethanol to produce a *Bezoar Bovis*-ethanol mixture,
   (c) combining gelatin and water to produce a gelation solution, and
   (d) combining said first filtrate, said *Bezoar Bovis* mixture and said gelatin solution to produce said pharmaceutical composition.

2. The process of claim 1, wherein the *Bezoar Bovis, Dioscoreae Rhizoma, Glycyrrhizae Radix, Ginseng Radix, Typhae Pollen, Massa Medicata Fermentata, Sojae germinatum Semen, Cinnamomi Cortex, Gelatin, Paeoniae Radix, Liriope Tuber, Scutellarae Radix, Angelicae Gigantis Radix, Ledebouriellae Radix, Atractylodis Rhizoma Alba, Bupleuri Radix, Platycodi Radix, Armeniacae Semen, Hoelen, Cnidii Rhizoma, Antellopis Cornu, Moschus, Borneol, Ampelopsis Radix,* and *Zingiberis Rhizoma* are present in an amount of about 45 parts, about 263 parts, about 188 parts, about 188 parts, about 94 parts, about 94 parts, about 94 parts, about 66 parts, about 66 parts, about 66 parts, about 56 parts, about 56 parts, about 56 parts, about 56 parts, about 56 parts, about 56 parts, about 47 parts, about 47 parts, about 47 parts, about 47 parts, about 47 parts, about 38 parts, about 38 parts, about 38 parts, about 28 parts and about 28 parts, by weight, respectively.

3. The process for preparing a pharmaceutical liquid composition of claim 1, wherein an aromatic agent, sweetening agent, emulsifier colloidal agent, suspension agent, and or preservative are further added to the pharmaceutical liquid composition.

4. The process for preparing a pharmaceutical liquid composition of claim 3, wherein the sweetening agent is ASPARTAME.

* * * * *